United States Patent [19]

Yarkony et al.

[11] Patent Number: 5,061,478
[45] Date of Patent: Oct. 29, 1991

[54] SPRAYABLE BIRD AND ANIMAL PEST REPELLANT COMPOSITION CONTAINING A TACKY POLYOLEFIN AND METHODS FOR THE PREPARATION AND USE THEREOF

[76] Inventors: Eitan Yarkony, Rehov Barket 12, Holon, Israel; Yair Yarkony, Rehov Rabinovitz 2, Kiryat Ben Gurion, Holon, Israel

[21] Appl. No.: 488,982

[22] Filed: Mar. 5, 1990

[30] Foreign Application Priority Data

Mar. 9, 1989 [IL] Israel ............................................ 89559

[51] Int. Cl.[5] ..................... A01M 29/00; A01N 25/02; A01N /25/06; C08J 123/18
[52] U.S. Cl. ........................................ 424/45; 424/407; 424/83; 514/918; 514/920; 524/579; 524/582; 524/583; 524/584
[58] Field of Search ....................... 424/45, 43, 78, 83; 514/770, 771, 918, 920; 524/579, 582-584

[56] References Cited

U.S. PATENT DOCUMENTS

| | | | |
|---|---|---|---|
| 3,306,817 | 2/1967 | Reinert | 424/83 |
| 3,335,051 | 8/1967 | Reinert et al. | 514/918 |
| 3,734,875 | 5/1973 | Sekuler | 524/579 |
| 4,294,730 | 10/1981 | Kenney | 524/522 |
| 4,348,385 | 9/1982 | Synek | 514/770 |
| 4,693,889 | 9/1987 | Chirchirillo et al. | 424/83 |
| 4,710,371 | 12/1987 | Palinczar | 424/47 |
| 4,873,082 | 10/1989 | Cacioli et al. | 424/83 |

*Primary Examiner*—Thurman K. Page
*Assistant Examiner*—Edward J. Webman
*Attorney, Agent, or Firm*—Staas & Halsey

[57] ABSTRACT

The invention provides a sprayable non-aqueous composition for repelling birds and animal pests, comprising a mixture of a tacky polyolefin, a substantially pure silica-based thixotropic agent and an organic solvent or diluent.

14 Claims, No Drawings

SPRAYABLE BIRD AND ANIMAL PEST REPELLANT COMPOSITION CONTAINING A TACKY POLYOLEFIN AND METHODS FOR THE PREPARATION AND USE THEREOF

The present invention relates to a sprayable bird and animal pest repellant composition and method.

The task of deterring birds from resting on exposed surfaces such as window sills, roofs and ledges of buildings, statues and other public edifices is a problem of major concern. The damage caused by birds runs into many millions of dollars each year, for example, to airplane hangars and other airfield installations, to telephone and other cables, to other exposed electrical equipment and in warehouses. Bird droppings are also considered to be a health hazard.

Thus, there is at the present day a need for a bird repellant composition which is convenient to use for both commercial and domestic applications, and which is weatherproof, that is to say, that it will be stable for an extended period of time when exposed to loci where birds are likely to roost or are known to roost. At the same time, such a composition should desirably be non-toxic to birds, pets, plants and humans. To the knowledge of the inventors, the only sprayable bird repellant which has been marketed hitherto is in the form of an aqueous emulsion which readily melts in hot weather and is washed away by rain. Other bird repellant compositions are smeared or painted on a surface, and do not have the convenience of a sprayable composition.

SUMMARY OF THE INVENTION

The present invention thus provides a sprayable non-aqueous composition for repelling birds and animal pests, which comprises a mixture of a tacky polyolefin, a substantially pure silica based thixotropic agent, and an organic solvent or diluent and which once applied is stable both in rain and sun for periods in excess of 12 months.

In another embodiment the present invention provides a method for repelling birds and animal pests from a locus, which comprises spraying onto the locus the sprayable composition recited above.

Thus, the present invention provides a composition which may be sprayed onto a locus where birds are known to roost, or where it is expected that they may roost. The present invention excludes the use of any ingredient which is toxic to humans. Preferably also, the invention excludes the use of any ingredient which is toxic to birds and animal pests. The repellent effect on birds and animal pests, when applying the composition according to the invention is due rather to its tackiness, which is sensed by the birds and animal pests when they touch the composition and imparts an insecure sensation which deters subsequent attempts.

The use of tacky polyolefins as animal and especially bird repellents is well known in the art.

Thus, e.g., in U.S. Pat. No. 3,306,817 from 1967 there is already described a method of repelling birds from a locus which comprises applying to said locus amorphous polypropylene in an amount sufficient to render said locus repellent to birds.

In more recent U.S. Pat. No. 4,693,889 there is described and claimed a bird repellent composition comprising 15-35 weight percent polyisobutylene having a Staudiner molecular weight of about 8,000 to 15,000. 20-50 weight percent paraffin oil, 0-15 weight percent isoparaffin oil, 0-6 weight percent organic modified montomorillonite and 15-45 weight percent kaolin clay.

Similarly in European Patent Applications 84109216.6 and 87101049.2 by the same applicants, published under publication numbers 0136468 and 0240656 respectively, there are described and claimed bird repellent compositions including an effective amount of a polymer component which polymeric component includes at least one butene polymer or copolymer and an effective amount of a thickening agent.

In the first of said European applications, the only thickening agent exemplified is Tixogel$^R$ which is an organophilic clay and in fact, in the second application the claim already is limited to a clay-based thickening agent.

Returning to the description in U.S. Pat. No. 3,306,817 it can be noted that in the examples in said patent, amorphous polypropylene was deposited on a roosting bar with a spatula.

In broadening language found in said patent it is stated that: "The amorphous polypropylene repellent of this invention can be applied to a locus from which birds are to be repelled by any suitable technique such as spraying, brushing, dusting and the like. Suitable aerosol containers having an inert propellent can also be used for conveniently dispensing the amorphous polypropylene. It is also within the scope of the invention to disperse the amorphous polypropylene in a volatile or a nonvolatile hydrocarbon or other organic solvent or dispersant. A suitable emulsifier can also be used for providing an aqueous dispersion of the repellent. To achieve a more uniform application of the repellent, it is generally preferred to apply it to the surface in a liquid carrier selected from the group consisting of water, acetone, kerosene, ethyl acetate, and isoparaffinic hydrocarbons which boil in the range of about 260° to about 800° F."

It is to be noted, however, that said patent does not exemplify or teach the manner in which a suitable aerosol can in fact be prepared. More importantly, following the bare suggestion of said patent one cannot obtain a satisfactory aerosol.

Thus, e.g. combining an amorphous polypropylene with a suitable solvent and propellant can result after due experimentation in a sprayable composition, however, such a composition does not remain on the locus sprayed and instead over a period of weeks, begins to evidence creep which both stains areas below those sprayed and reduces the repellent properties of the area initially sprayed until as said creep progresses, the originally sprayed area no longer possesses bird repellent properties.

Preparation of an aqueous dispersion by introducing a suitable emulsifier as suggested by said patent is found to be even less effective in practice since such a composition is soon washed away by rain.

Due to the lack of an enabling teaching in said patent and the apparent difficulties with preparing a suitable sprayable bird repellant composition, in the more than twenty years that has elapsed since the publication of said patent, no literature of which applicant is aware has again suggested, let alone taught, the application of a tacky bird repellent composition by spraying, despite the wide felt need for such a composition and the obvious advantages thereof.

Thus, e.g. more recent U.S. Pat. No. 4,693,889 teaches the preparation of a gel to be applied by means of a caulking gun and the above-mentioned European applications teach bird repellent compositions in a gel, bead or strip form for delivery in cartridges.

As will be realized, gels delivered with caulking guns or with cartridges are extremely time-consuming to apply on large areas and on the other hand, are not readily applicable for domestic use such as by householders troubled by pigeons which roost on their windowsills or the eaves of their homes.

While thixotropic agents in general and silica based thixotropic agents in particular, have been known for decades, heretofor it has not been suggested in the literature to combine thixotropic agents with tacky polyolefins to produce a bird repellent which can be sprayed on desired surfaces and which readily flows through the spray nozzle but then immediately coagulates upon contact with the sprayed surface without exhibiting creep even at temperatures of up to 130° C.

The silica based thixotropic agents found to be effective in the compositions of the present invention are those available on the market and described as highly dispersed, highly pure amorphous silica. Especially preferred are CAB.O.SIL$^R$ fumed silica of Cabot Corp. U.S. and Aerosil$^R$ of Degussa.

As stated, the tacky component of the present composition can be any of the tacky polyolefins known and used for this purpose, however, especially preferred are tacky poly($C_4$-olefins) and most preferred is tacky polybutene, e.g. polybutene of a molecular weight of about 2300.

The organic solvent or diluent may comprise, e.g., at least one member selected from aliphatic hydrocarbons, aromatic hydrocarbons, alicyclic hydrocarbons, halogenated hydrocarbons, aliphatic alcohols, esters and ketones. It will be appreciated that the principal function of the solvent or diluent on the one hand, is to make the composition easier to handle than it would be without any solvent or diluent, but that on the other hand, the solvent or diluent will be desirably one which will readily evaporate when exposed to ambient conditions, leaving the mixture of other components which will be relatively stable under diverse conditions of weather (for periods of up to 12 months or more) and will therefore be effective to repel birds and animal pests for a long period of time.

A first manner of applying the compositions of the present invention, especially on large surfaces is by pressurization from an essentially non-disposable refillable container, e.g., by pumping in air or other propellant at superatmospheric pressure, or by using airless spraying equipment. It will be appreciated that in principle any known types of spraying equipment may be used. An example of an air spraying system is constituted by the "Sagola" spray gun model no. 4036, with 2.80 mm. tip, air cap no. 62-S, working pressure 35–60 psi, the air consumption at 50 psi being approximately 292 liters/minute. An example of an airless spraying system is the trolley-supported "Wagner" 207E, nozzle 0.013/10°, 100 mesh gun filter, working pressure 100 bar, flow volume 0.570 liter/minute.

When seeking to cover a large area, then by way of example only, the composition of the invention may be sprayed in parallel lines (for example, about 5–20 cm. wide), separated by e.g., about 2–3 cm. to spray the composition of the invention, in an amount such that after evaporation of the solvent, the thickness of the sprayed layer will be, e.g., approximately 1 mm.

Such a composition can comprise by weight about 25 to 95% tacky polyolefin, about 0.5 to 6% silica-based thixotropic agent and 5 to 75% solvent.

While high molecular weight polybutene is preferred for use in the present compositions because of its greater stability, when making formulations with higher percentages of polyolefin, e.g., about .70%, then lower weight polyolefins are preferably used, e.g., polybutene of a molecular weight of between 900 and 1000.

Preferred compositions will comprise about 40 to 70% tacky polyolefin, 1.5 to 4% silica-based thixotropic agent and about 15 to 25% solvent.

The present invention also provides a method for preparing a sprayable non-aqueous composition for repelling birds comprising combining (based on weight of final composition) about 5 to 75% by weight of a solvent as herein defined and about 0.5 to 6% silica-based thixotropic agent and then slowly adding at substantially ambient temperature, 25 to 95% of the tacky polyolefin.

The present method obviates the need for heating and the cost involved therein which characterized the prior art processes described e.g., in European applications 84109216.6 and 87101049.2.

In an especially preferred embodiment of the present invention, there is provided an aerosol composition comprising a tacky polyolefin, a substantially pure silica based thixotropic agent, an organic solvent or diluent and a propellant.

When a propellant is present in the composition, this may comprise at least one component selected from carbon dioxide, nitrous oxide, argon, nitrogen, oxygen and mixtures thereof, such as for example, air. In the alternative, a propellant may comprise at least one member selected from propane, butane, isobutane, trichloromonofluoromethane, dichlorodifluoromethane, difluoromonochloromethane, difluoromonochloroethane, dichlorotetrafluoroethane, dichlorotrifluoroethane, monobromomonochlorodifluoroethane, monobromotrifluoromethane, trichlorotrifluoroethane, tetrafluoroethane, octafluorocyclobutene and dimethyl ether or mixtures thereof. As an example of mixtures, a propane/butane mixture in the range of about 10:90 to about 40:60 e.g., 20:80 o 25:75, may be used. Higher-boiling materials such as e.g., pentane and hexane which would be unsuitable for use as propellants on their own, could possibly be used as ingredients of propellant mixtures with lower-boiling components. In view of the flammability of hydrocarbon propellants and of dimethyl ether, and their explosive potentiality when admixed with oxygen, the usual precautions should be exercised when using these materials. Where there is no objection to the use of fluorocarbons (which are usually non-flammable) as propellants, it is particularly preferred that such propellant comprises a mixture of dichlorodifluoromethane and dichlorotetrafluoroethane. Insofar as certain countries, states and local authorities may have enacted legislation prohibiting the use of at least certain of fluorinated hydrocarbons as propellants due to a belief that they may cause irrevocable damage to the ozone layer, the present disclosure is not intended to invite use of such propellants contrary to this legislation. Indeed, the attention of the skilled person is directed to the alternative propellants which may be used in accordance with the invention.

It will be appreciated that propellants about which concern has been expressed with regard to potential damage to the ozone layer are perhalogenated, i.e., fully halogenated, fluorinated hydrocarbons. Consequently there is at the present time a continuing interest in fluorinated hydrocarbon propellants which are not fully halogenated, such as 1,1,1,2-tetrafluoroethane, 1,1-dichloro-2,2,2-trifluoroethane, difluoromonochloromethane and 1-chloro-1,1-difluoroethane.

A particular hazard in the case of ethers such as dimethyl ether, is the possibility of forming explosive peroxides; therefore, such propellants should not be used in the absence of effective peroxide formation inhibitors.

Especially preferred for use in the aerosol compositions of the present invention are propellants which themselves are solvents for the tacky pololefins and which immediately evaporate once sprayed.

Aliphatic hydrocarbon propellants are thus especially preferred such as the mixtures of propane/butane mentioned above.

A preferred aerosol propellant pressurized sprayable composition according to the present invention will comprise by weight about about 25 to 95% tacky poyolefin, about 0.5 to 6% silica-based thixotropic agent, about 5 to 70% solvent and about 5 to 75% propellant.

Especially preferred is an aerosol composition comprising by weight about 40 to 70% tacky polyolefin, about 1.5 to 4% silica-based thixotropic agent, about 15 to 25% solvent and about 5 to 30% propellant.

A most preferred aerosol composition comprises about 50 to 55% polybutene, 2 to 3.5% silica-based thixotropic agent, 25 to 35% solvent and 14 to 18% propellant.

It is to be understood that in general, any types of aerosol containers, which are known to those skilled in the art may be utilized in applying the present invention. Reference may be made, by way of example, to Sanders, Handbook of Aerosol Technology, Van Nostrand Reinhold Company, 2nd Edition 1979, the disclosures of which are incorporated herein by reference.

A new type of aerosol container which has recently appeared on the market is the two-compartment piston can in which the product is filled from the top and the propellant from the bottom wherein the product in the compartment above the piston is under pressure from the propellant which remains in the bottom part of the can throughout use, and such containers can also be used.

As will be realized, the composition of the invention may be applied by spraying to any locus, from which it is desired to repel birds and animal pests. By way of example, the compositions may be sprayed onto roofs, airplane hangars, antennas, parabolic antennas and reflectors, solar heaters, ventilation ducts, air conditioners, roofing beams, window ledges, sheds and other buildings, and exposed electrical installations such as power lines and transformers at airports and in warehouses, and anywhere else, especially where it is known that birds roost or nest. It will be appreciated that while the present invention is especially directed to repelling birds, it will also be effective to repel animal pests (including crawling insects such as ants) and in particular, e.g., reptiles and rodents, especially tree-climbing pests which damage fruit such as squirrels or hyrax, in which case the composition can be, e.g., sprayed around the base of a tree or on the tree-trunk.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE I

In accordance with substantially known industrial procedures, a standard aerosol can of approximately 250–300 cc. capacity was filled with an admixture of 100 g. composition [comprising approximately 37 g. tacky polybutene, 61 g. 1,1,1-trichloroethane and 2 wt. % highly dispersed silica (Aerosil 200)] and as propellant, 34 g. 80:20 butene-propane mixture.

This composition, after spraying on a locus and evaporation of the solvent, has been found to be stable under diverse weather conditions for not less than 12 months.

EXAMPLE II

The following composition may be used in place of the admixture of Example I, namely, 100 g. composition [comprising approximately 3 g. polyisobutylene (Vistanex L 120, Exxon Chemicals Co.), 25 g. tacky polybutene "H-100", 10 g. glycerol ester of hydrogenated rosin, 30 g. 1,1,1-trichloroethane, 30 g. methylene chloride and 2 wt. % highly dispersed silica (Aerosil 200)] and as propellant, 34 g. 80:20 butene-propane mixture.

EXAMPLE III

In accordance with substantially known industrial procedures, a standard aerosol can of approximately 200 c.c. capacity was filled with an admixture of 90 g. composition [comprising approximately 50 wt % tacky polybutene, 48 wt. % solvent (1,1,1-trichloroethane or a 50:50 admixture of 1,1,1-trichloroethane with methylene chloride) and 2 wt. % highly dispersed silica] and a propellant which comprised dichloro-difluoromethane (4 g.) and dichlorotetrafluoroethene (6 g.)].

EXAMPLE IV

The following composition may be used in place of the admixture of Example III, namely, 95 g. composition (comprising approximately 50 wt. % tacky polybutene, 48 wt. % solvent (1,1,1-trichloroethane or a 50:50 admixture of 1,1,1-trichloroethane with methylene chloride) and 2 wt. % highly dispersed silica) and a propellant which comprised butene (3.75 g.) and propane (1.25 g.).

The foregoing exemplified compositions, minus propellants are also suitable for large scale application by either systems not requiring propellant (e.g. "airless") or air-pressurized spraying systems.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A sprayable non-aqueous composition for repelling birds and animal pests consisting essentially of about 25 to 95% tacky polyolefin, about 0.5 to 6% silica-based thixotropic agent and 5 to 75% solvent by weight, which combination of thixotropic agent and solvent enables said composition to readily flow through a spray nozzle and then immediately coagulate upon contact with a sprayed surface without exhibiting creep even at temperatures of up to 130° C.

2. A sprayable non-aqueous composition for repelling birds and animal pests according to claim 1, wherein said tacky polyolefin is tacky polypropylene, tacky polyisobutylene or tacky polybutene.

3. A sprayable non-aqueous composition for repelling birds and animal pests according to claim 1, wherein said tacky polyolefin is tacky polybutene.

4. A sprayable non-aqueous composition for repelling birds and animal pests according to claim 1, consisting essentially of by weight about 40 to 70% tacky polyolefin, 1.5 to 4% silica-based thixotropic agent and about 15 to 25% solvent.

5. An aerosol propellant pressurized sprayable non-aqueous composition for repelling birds and animal pests according to claim 1, consisting essentially of by weight about 25 to 95% tacky polyolefin, about 0.5 to 6% silica-based thixotropic agent, about 5 to 70% solvent and about 5 to 75% propellant.

6. An aerosol propellant pressurized sprayable non-aqueous composition according to claim 5 wherein said propellant comprises at least one aliphatic hydrocarbon propellant which is a solvent for said tacky polyolefin.

7. A method for repelling birds and animal pests from a locus, which comprises applying by spraying onto the locus from a disposable aerosol container a sprayable aerosol propellant composition as defined in claim 6.

8. An aerosol propellant pressurized sprayable non-aqueous composition according to claim 6 wherein said propellant comprises a mixture of propane and butane.

9. A method for repelling birds and animal pests from a locus, which comprises applying by spraying onto the locus from a disposable aerosol container a sprayable aerosol propellant composition as defined in claim 8.

10. A method for repelling birds and animal pests from a locus, which comprises applying by spraying onto the locus from a disposable aerosol container a sprayable aerosol propellant composition as defined in claim 5.

11. A method for repelling birds and animals pests from a locus, which comprises applying by spraying onto the locus a sprayable composition according to claim 1.

12. A method according to claim 11 wherein the composition is applied by pressurization from a non-disposable refillable container.

13. A method according to claim 11, wherein the pressurization is supplied by a propellant-pressurized system.

14. A method for preparing a sprayable non-aqueous composition for repelling birds consisting essentially of combining about 5 to 75% by weight of an organic solvent or diluent and about 0.5 to 6% of a silica-based thixotropic agent, said weight percentage being based on the final composition and then adding thereto at ambient temperature about 25 to 95% of a tacky polyolefin.

* * * * *